United States Patent [19]

Fletcher et al.

[11] 4,055,072
[45] Oct. 25, 1977

[54] APPARATUS FOR MEASURING A SORBATE DISPERSED IN A FLUID STREAM

[76] Inventors: James C. Fletcher, Administrator of the National Aeronautics and Space Administration, with respect to an invention of; Otis L. Updike, Charlottesville, Va.

[21] Appl. No.: 615,030

[22] Filed: Sept. 19, 1975

[51] Int. Cl.$^2$ ............................................. G01N 31/06
[52] U.S. Cl. ........................................................ 73/23
[58] Field of Search .............. 73/23, 67, 67.2, DIG. 2; 357/26.25, 232 R, 232 E, 254 R, 254 E; 333/30 R

[56] References Cited

U.S. PATENT DOCUMENTS

| | | | |
|---|---|---|---|
| 3,260,104 | 7/1966 | King | 73/23 |
| 3,479,572 | 11/1969 | Pokorny | 357/26 |
| 3,686,579 | 8/1972 | Everett | 357/26 |
| 3,792,321 | 2/1974 | Seifert | 357/26 |
| 3,828,607 | 8/1974 | Janzen et al. | 73/23 |
| 3,831,432 | 8/1974 | Cox | 73/23 |
| 3,879,992 | 4/1975 | Bartera | 73/23 |

*Primary Examiner*—Jerry W. Myracle
*Assistant Examiner*—Stephen A. Kreitman

*Attorney, Agent, or Firm*—John R. Manning; Darrell G. Brekke

[57] ABSTRACT

An apparatus for measuring a sorbate dispersed or dissolved in a fluid stream and comprising an oscillator for generating a first alternating-current signal, an acoustic transmission line for disposition in the fluid stream and including an elongated body having a surface capable of sorbing an amount of the sorbate to be measured representative of the concentration thereof in the fluid stream, the body being capable of propagating acoustic energy along its length from one end portion to another end portion, the propagated acoustic energy being damped in amplitude and shifted in phase such that the change in amplitude or phase is proportional to the amount of sorbate sorbed by the surface, a first transducer for converting the alternating current signal to acoustic energy and for applying the acoustic energy to the one end portion, a second transducer for converting the acoustic energy propagated to the other end portion to a corresponding electrical signal, and a comparator for comparing the electrical signal to the alternating-current signal for developing an output signal corresponding to a difference therebetween, the output signal being indicative of the concentration of the sorbate in the fluid stream.

13 Claims, 9 Drawing Figures

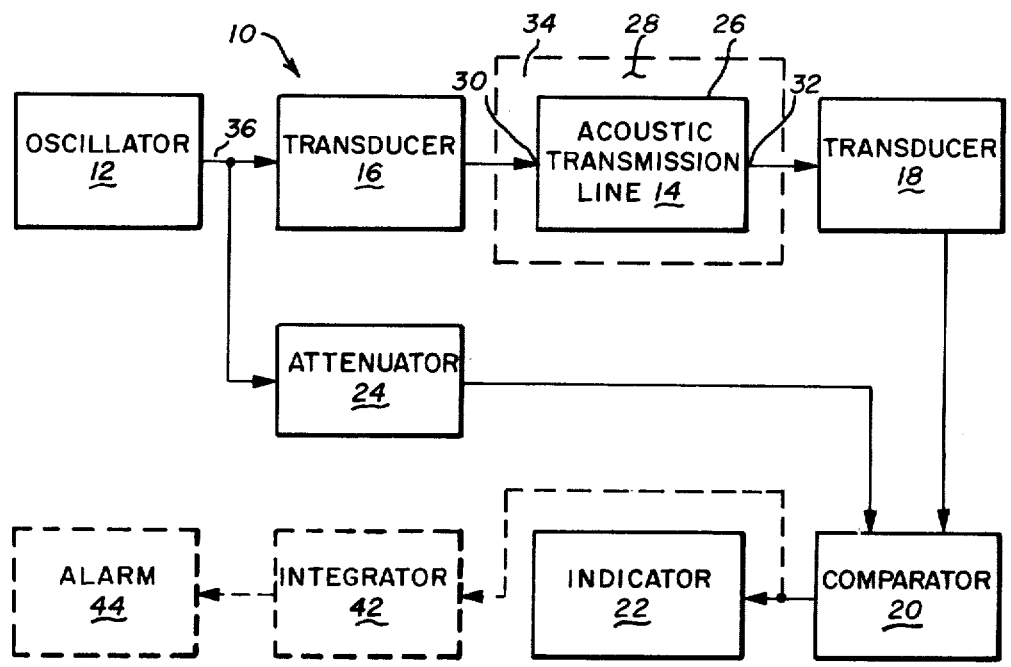
Fig_1
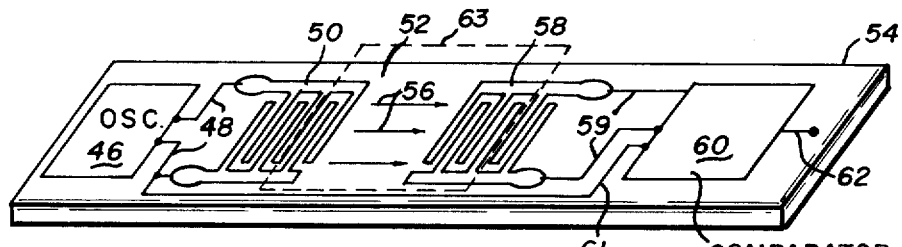
Fig_2
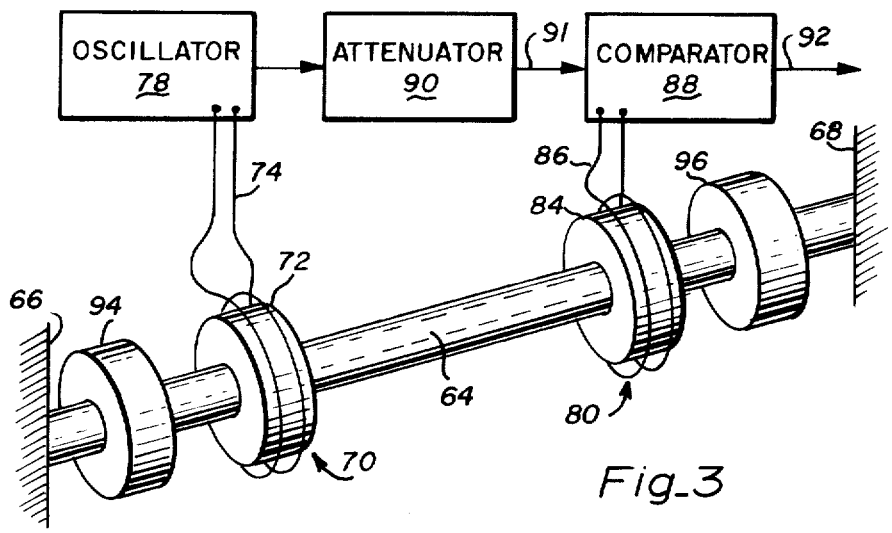
Fig_3

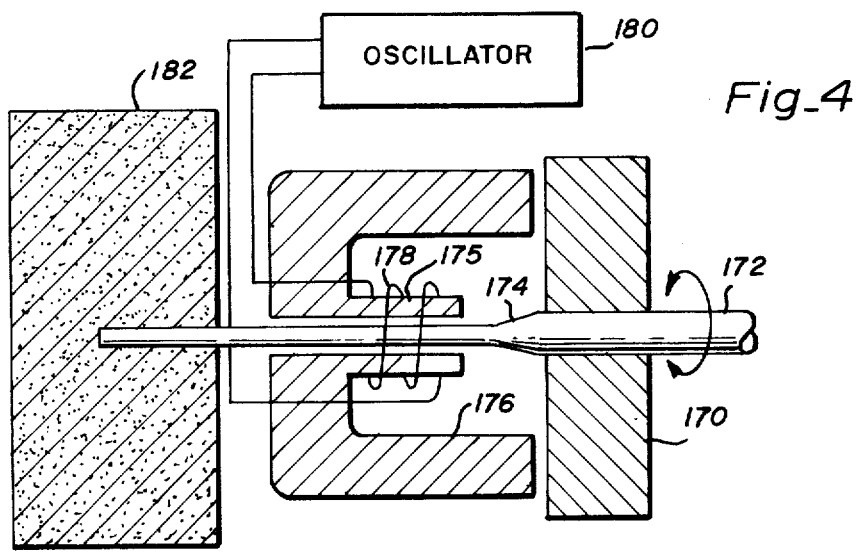
Fig_4
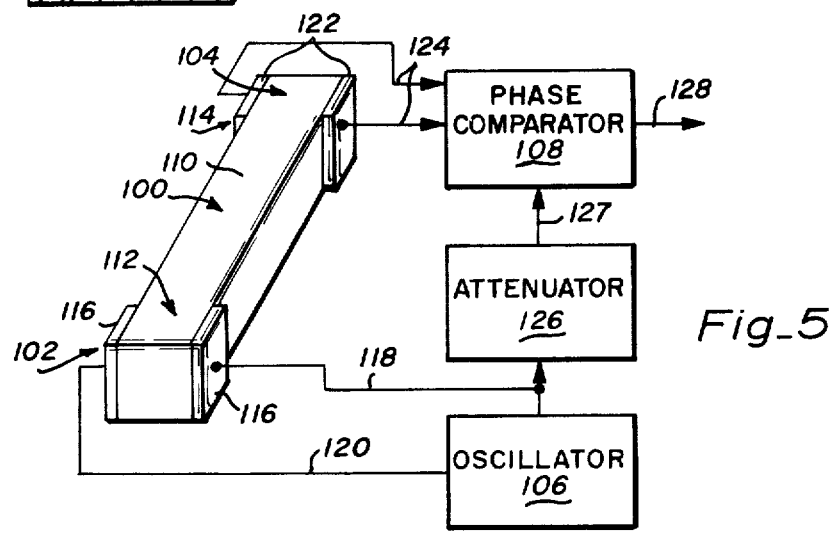
Fig_5
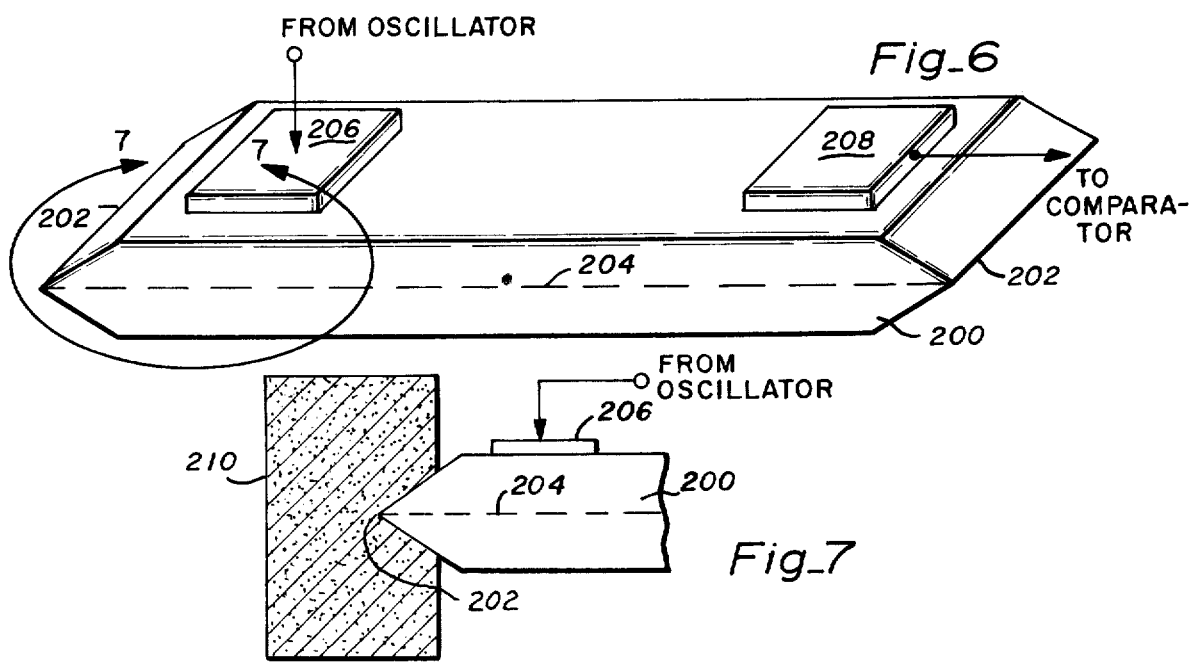
Fig_6
Fig_7

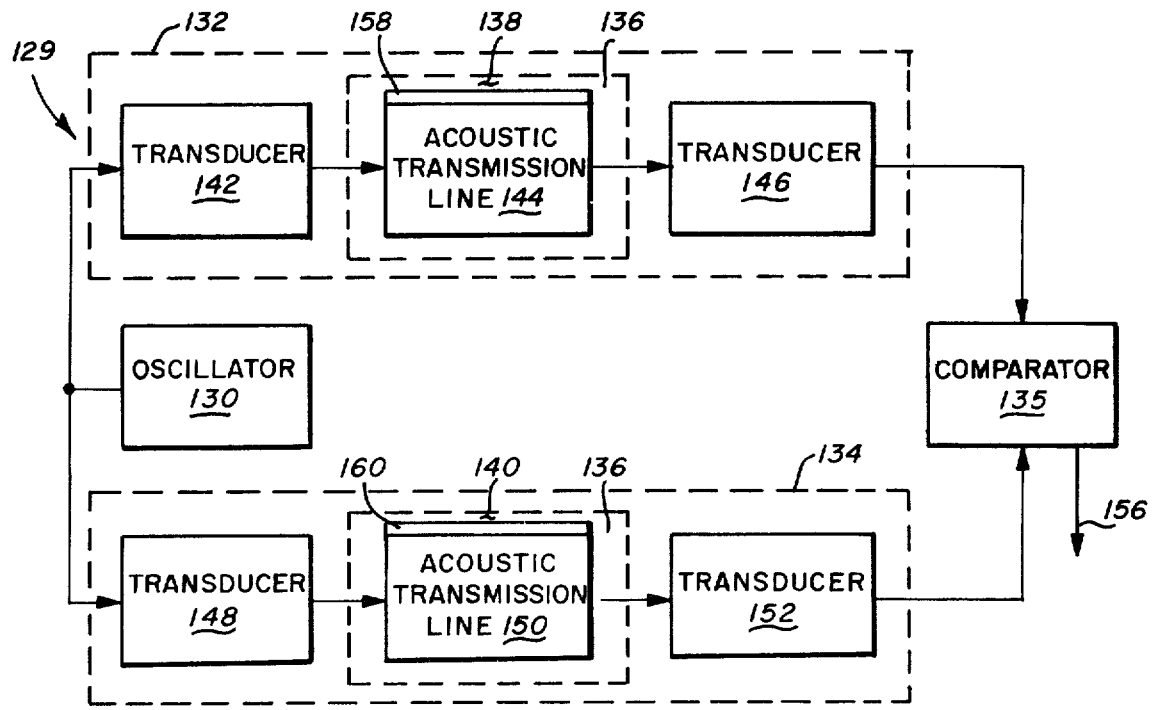
Fig_8
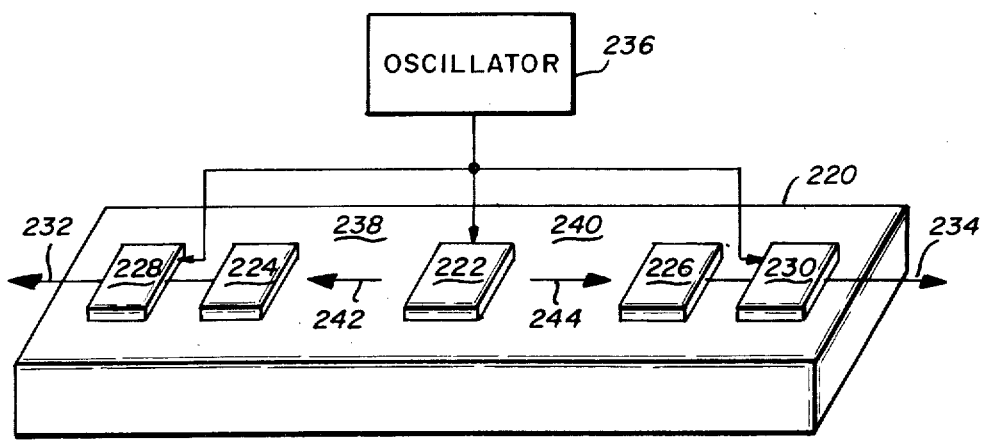
Fig_9

APPARATUS FOR MEASURING A SORBATE DISPERSED IN A FLUID STREAM

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates generally to fluid analyzers, and more particularly to a fluid analyzer for measuring the concentration of a sorbate dispersed in a fluid stream.

2. Description of the Prior Art

Many devices are available for detecting concentrations of substances dispersed in a fluid stream. An example of such a device is found in the articles entitled "Using Quartz Crystals as Sorption Detectors" by William H King, Jr., *Research/Development*, in the April 1969 volume at page 28 and in the May 1969 volume at page 28. The device described therein employs a piezoelectric crystal as a resonator in an electronic oscillator. When the device is placed in a fluid stream, the sorbed mass of a sensed sorbate is accumulated on the crystal, causing the quantity of resonating mass to increase. A disadvantage of such a device is that as the resonating mass increases, the amplitude of a sensed signal may be nonreproducible in the presence of sorbate on the crystal. Other drawbacks of this device are that its sensitivity is limited by the noise of the oscillator and the noise in an associated frequency-sensing discriminator.

Examples of other related prior art detection systems can be found in U.S. Pat. No. 3,260,104, to W. H. King, Jr.; U.S. Pat. No. 3,266,291 to W. H. King, Jr.; U.S. Pat. No. 3,327,519 to H. M. Crawford; U.S. Pat. No. 3,329,004 to W. H. King, Jr.; and U.S. Pat. No. 3,828,607 to D. W. Janzen and C. G. Dell.

SUMMARY OF THE INVENTION

It is therefore a principal object of the present invention to provide an apparatus for measuring low concentrations of a sorbate dispersed in a fluid stream and for providing such an apparatus which is miniature in size, has a high sensitivity and may be fabricated at low cost.

Briefly, the present invention comprises an electronic oscillator for generating a first alternating-current signal, an acoustic transmission line for disposition in the fluid stream and including an elongated body having a surface capable of sorbing an amount of the sorbate to be detected commensurate with the concentration thereof in the fluid stream, the body being capable of propagating acoustic energy along its length from one end portion to another end portion, the propagated acoustic energy being damped in amplitude and shifted in phase such that the change in amplitude and phase is proportional to the amount of sorbate sorbed by the surface, a first transducer for converting the alternating-current signal to acoustic energy and for applying the acoustic energy to the one end portion, a second transducer for converting the acoustic energy propagated to the other end portion to a corresponding electrical signal, and a comparator for comparing the electrical signal to the alternating-current signal and for developing an output signal coresponding to a difference therebetween, the output signal being indicative of the concentration of the sorbate in the fluid stream.

An advantage of the present invention is that the apparatus can be designed to exhibit high sensitivity to extremely small amounts of sorbate dispersed in a fluid stream and to exhibit low sensitivity to large amounts of sorbate.

Another advantage of the present invention is that the apparatus may be formed in a microminiature size and at a low cost using bath microfabrication technology.

Still another advantage of the present invention is that the frequency of oscillation of the reference signal source employed is not effected by the mass of the sorbate, and lower noise levels may be achieved by separation of the oscillator subsystem from the sensing subsystem.

Yet another advantage is that separation of the oscillator subsystem from the sensing subsystem allows the use of a wide variety of substrates and configurations for the sensing subsystem, hence permitting optimization of the sorption function and of the oscillator function as well.

The foregoing and other objects, features and advantages of the invention will be apparent from the following detailed description of the preferred embodiments illustrated in the several figures of the drawing.

IN THE DRAWINGS

FIG. 1 is a block diagram generally illustrating an apparatus in accordance with the present invention for detecting a sorbate dispersed in a fluid stream;

FIG. 2 is a perspective representation of the preferred embodiment of the apparatus illustrated in FIG. 1 with several of the components of the apparatus shown schematically;

FIG. 3 is a perspective view of an alternative embodiment of the apparatus illustrated in FIG. 1 with several of the components of the apparatus shown schematically;

FIG. 4 is a cross-sectional view of an alternative embodiment of the magnetostrictive driver of FIG. 3;

FIG. 5 is a perspective view of yet another alternative embodiment of the apparatus illustrated in FIG. 1 with several of the components of the apparatus shown schematically;

FIGS. 6 and 7 are a perspective view and a partial side elevation view of an alternative embodiment of the apparatus illustrated in FIG. 5; and FIGS. 8 and 9 are block diagrams generally illustrating still other alternative embodiments of the apparatus illustrated in FIG. 1.

DESCRIPTION OF THE PREFERRED EMBODIMENT

Referring now to FIG. 1 of the drawing, there is shown a generalized block diagram of an apparatus for measuring a sorbate dispersed in a fluid stream referred to generally by the numeral 10. The apparatus 10 includes an electronic oscillator 12, an acoustic transmission line 14, transducers 16 and 18, comparator 20, an indicator 22, and an attenuator 24.

The oscillator 12 includes those components required to generate an alternating current electrical signal having a frequency which is substantially constant in time and does not drift. In the preferred embodiment the oscillator 12 is designed to have an extremely low random phase fluctuation such that very little phase noise is produced on the generated signal.

The acoustic transmission line 14 is an elongated body having an exterior surface 26 capable of sorbing an amount of a sorbate, generally illustrated by the numeral 28, to be measured. The body is capable of propagating acoustic energy along its length from one end portion 30 to another end portion 32 and is disposed in a fluid stream, generally shown in dashed lines and referred to by the numeral 34. As used in this application, sorbate is defined as a gas or sorbable component, substance or particle of a gas or aerosol taken up by a sorbent; a sorbent is the material which takes up the sorbate by sorption; and sorption is the taking up of a sorbate by absorption or adsorption. It should also be recognized that mass loading of the body may also be changed by impingement, erosion and additive or substrative chemical reactions. Dispersion is defined as including both molecular and particulate dispersion. The propagated acoustic energy is damped in amplitude and shifted in phase such that the change in amplitude and/or phase is proportional to the amount or sorbate sorbed by the surface 26.

The output of the oscillator 12 is connected by a propagation path such as a conductor 36 to the transducer 16 which converts the alternating-current signal to acoustic energy. The output of the transducer 16 is coupled to the end portion 30.

The transducer 18 has an input coupled to the end portion 32 and serves to convert the acoustic energy received therefrom into an alternating current electrical signal having the same frequency as the signal generated by the oscillator 12.

In the preferred embodiment, the oscillator 12, transmission line 14, and transducers 16 and 18 operate in the 10–1000 MHz frequency band. It should be recognized that for high sensitivity performance, the transmission line is at least several and perhaps up to 100 acoustic wavelengths in length, and also that by choosing the line length, the sensitivity can be controlled for a wide range of solute (sorbate) concentrations and sorbent affinities. Accordingly, at frequencies in the 10–1000 MHz band, the physical size of the transmission line is relatively small. In addition, in the preferred embodiment, the acoustic energy serves to produce motional crests such as surface waves, at the surface 26 in the direction of propagation.

The attenuator 24 is connected between the conductor 36 and the reference input of the comparator 20 and serves to decrease the amplitude of the generated signal to a level appropriate for comparison with the signal developed by the transducer 16.

The comparator 20 may take the form of any suitable device capable of comparing the output of transducer 18 to the output of attenuator 24 to develop an output signal corresponding to a difference therebetween. In the preferred embodiment, the detector 20 is a phase detector that develops an output signal corresponding to the difference in phase between the signals and is calibrated to provide an output signal which varies approximately linearly with respect to the mass of sorbate 28 sorbed on the surface 26. Alternatively, the comparator 20 could be an amplitude detector that develops an output signal corresponding to the difference in amplitude between the signals. In either alternative embodiment, the attenuator may be omitted from the apparatus.

The indicator 22 is coupled to the output of the comparator 20 and displays the output signal. The indicator 22 may take the form of any suitable device capable of displaying this signal, such as a meter, recorder, computer input port, oscilloscope, etc.

In operation, the elongated body 14 is placed in the fluid stream 34 including the sorbate 28, the concentration of which is to be measured. Energization of the oscillator 12 causes the oscillator to generate a reference signal having a constant frequency. The reference signal is applied through the attenuator 24 to provide a predetermined signal level at the reference input of the phase comparator 20. Simultaneously, the reference signal is applied to the transducer 16 which converts it into acoustic energy and applies the energy to the input end portion 30 of the body 14. As the concentration of the sorbate 28 increases, the quantity of sorbed mass on the surface 26 likewise increases. Accordingly, as the energy propagates through the length of the body, it is damped in amplitude and shifted in phase representative of the amount of sorbate sorbed by the surface 26. The increased sorbed mass changes the ratio of inertance to compliance for the effective transmission mode associated with the transmission line 14, thus altering the phase, and further alters the dissipative effects, thus changing the amplitude of the acoustic wave between the end portions 30 and 32. As the acoustic wave reaches end portion 32, it is converted into an electrical signal by transducer 18 and the electrical signal is applied to the second input of the phase comparator 20. Phase comparator 20 then compares the phase of that signal with the phase of the reference signal and develops an output signal corresponding to any difference. The output signal is then input to the indicator 22 for display. By selectively calibrating phase comparator 20 and indicator 22, the concentration of the sorbate 28 in the fluid stream 34 is indicated directly.

An additional feature, illustrated by dashed lines in FIG. 1, includes an integrator 42 which is connected to the output of the comparator 20 and serves to sense the cumulative amount of the sorbate 28 in the fluid stream 34 over a period of time. An alarm 44, such as a buzzer or a light, is connected to the output of the integrator 42 and provides an indication when the cumulative amount of the sorbate exceeds a predetermined level. This feature lends itself well to applications in which the quantity of toxic or noxious gases in a confined volume, such as in a space capsule, must be monitored, and to integration of concentration peaks in a gas chromatograph effluent stream.

Referring now to FIG. 2, a representative physical embodiment of the present invention is illustrated. As shown, an oscillator circuit 46, input transducer 50, output transducer 58 and comparator circuit 60 are formed on the surface 52 of a piezoelectric substrate 54. It should be noted, however, that the substrate is not necessarily piezoelectric; overlay and other types of transducers can excite surface acoustic waves in nonpiezoelectric substrates (e.g., silicon). The output of oscillator 46 is connected by conductors 48, one of which may be grounded, to the comb-shaped interdigital transducer array 50 formed on surface 52 of the elongated substrate 54. The construction and operation of piezoelectric devices are particularly described in detail in a publication entitled "Practical Surface Acoustic Wave Devices" by Melvin G. Holland and Louis T. Claiborne, *Proceedings of the I.E.E.E.*, Volume 62, No. 4, May 1974, at page 582. In the preferred embodiment, the substrate 54 is formed from quartz. Alternatively, other materials with low temperature coefficients of propagation velocity may be used.

In response to the alternating voltage applied to its input by oscillator 46, the transducer array 50 causes the piezoelectric material between the fingers of the array to periodically distort. This periodic distortion produces an acoustic energy wave having the same frequency as that of the oscillator signal and which propagates away from the array 50 along the surface 52 in the direction of the arrows 56.

The output interdigital transducer array 58, which is similar to the array 50, cooperates with the continuous piezoelectric material to convert the periodic distortion of the substrate 54 back into an electrical signal. The phase comparator 60 is connected to the output terminals of the array 58 by conductors 59 and to the output of oscillator 46 by a conductor 61. The output of comparator 60 is taken at an output terminal 62.

In the preferred embodiment, the sorbate 28 disposed on the surface 52 is adsorbed, and accordingly, the surface 52 is cleaned, such as by etching or ion bombardment, to improve the surface affinity for the sorbate. Alternatively, the sorbate is absorbed, and accordingly, an appropriate film, illustrated schematically by the dashed lines 63, of a low volatility solvent of the component of interest is applied, such as by vacuum evaporation, in a covering relationship to the surface 52. The film 63 characteristically absorbs or reacts with the sorbate of interest preferentially to others in the fluid stream. Selective sorbents are known for a great many sorbates from the technology of gas chromatography.

Referring to FIG. 3, another alternate embodiment of the present invention is illustrated. As shown therein, a length of wire or a stiff rod 64, is supported in a stable configuration, e.g., in axial tension or compression, between mounts 66 and 68 in a fluid stream containing the sorbate to be measured. An input magnetostrictive transducer 70 comprising a toroid 72 formed from magnetic material and a winding 74 coiled coaxially therearound is disposed around and secured mechanically by adhesive bonding, e.g., cementing, to an input portion of the wire 64. The winding 74 is spaced from the toroid 72 and thus does not mechanically load it during operation. The terminals of the winding 74 are connected to an electronic oscillator 78. The winding 74 serves to convert the alternating current produced by the oscillator 78 into an alternating magnetic field which is substantially contained in the toroid 72. The transducer 70 responds to the alternating magnetic field and causes the wire 64 to torsionally vibrate. The vibration is propagated down the length of the wire toward the mount 68 with the motional crests occurring at the surface of the wire 64 so that the sensitivity of mass loading is greatest.

An output magnetostrictive transducer 80 is disposed around and secured mechanically by adhesive bonding to an output portion of the wire 64. The transducer 80 is constructed similarly to the transducer 70 and comprises a magnetic toroid 84 and a coaxial winding 86. An input of phase comparator 88 is connected to the terminals of the winding 86. An output of oscillator 78 is connected through an attenuator 90 and a conductor 91 to another input of comparator 88. The output of comparator 88 is taken to an output terminal 2. A pair of cylindrically-shaped dampers 94 and 96 are mounted on the wire 64 intermediate the respective mounts and magnetostrictive transducers and spaced from the transducer, preferably by a distance of a quarter wavelength. The dampers 94 and 96 serve to prevent the torsional vibrations of the wire from reaching and being reflected from the mounts and thus acoustically isolate the output portion of the wire 64 from variable loading effects of the mountings. A film (not shown) may be applied to the external surface of the wire 64 when it is desired to absorb the sorbate.

In operation, energization of the winding 74 with an alternating current by the oscillator 78 causes an alternating magnetic field to be set up in the toroid 72 which in turn causes the wire 64 to torsionally vibrate. As the concentration of sorbate in the fluid stream increases, the quantity of sorbed mass on the surface of the wire 64 also increases. Hence, the torsional vibration propagating along the surface of the wire 64 toward its output portion is decreased in amplitude and shifted in phase such that the change in amplitude and phase is proportional to the amount of sorbate sorbed by the surface. As the torsional vibration reaches the output portion, it is converted into a corresponding electrical signal by the transducer 80. Phase comparator 88 compares the phase of the electrical signal with the attenuated reference signal on conductor 91 and provides an output on terminal 92.

An alternative embodiment of a magnetostrictive transducer is illustrated in FIG. 4. As shown, a ferrite magnetostrictive toroid 170 is cemented to a rod 172 which may be in either tension or compression. The rod 172 serves to propagate torsional vibrations and has a tapered end 174 to reduce reflections. The rod 172 passes through a central opening in a hollow cylindrical portion 175 of a cup-shaped ferrite core 176. A winding 178 is coiled coaxially around and spaced from the cylindrical portion 175 and when energized serves to provide a longitudinal flux in the rod without loading it. The terminals of the winding 178 are connected to an electronic oscillator 180 which serves to energize the winding. The end 174 is supported by a viscoelastic block 182 which serves to absorb torsional energy propagated through the tapered end of the rod. In the preferred embodiment, the block is comprised of silicon rubber, although certain types of grease may also be used. When energized by the oscillator 180, the winding 178 sets up a longitudinal magnetic flux in the cylindrical portion and a tangential magnetic flux in the toroid 170 which combine to produce a torsional vibration in the rod 172.

Referring now to FIG. 5, yet another embodiment of the present invention is illustrated. As shown, the apparatus comprises an elongated body 100 formed from a material having acoustic transmission properties, an input transducer 102, an output transducer 104, an oscillator 106 and a comparator 108. The body 100 may be formed from piezoelectric material and includes an exterior surface 110 capable of sorbing an amount of a sorbate, an input portion 112 and an output portion 114 and is adapted to be disposed in a fluid stream. The input transducer 102 comprises a pair of conductive plates 116 disposed on opposite parallel surfaces of the input portion 112. The output terminals of oscillator 106 are connected by conductors 118 and 120 to the respective plates 116. The oscillator 106 produces an alternating voltage across the plates 116, which in turn provide an alternating electric field therebetween.

In response to the alternating electric field, the input portion 112 undergoes a shearing vibration with motional maxima at the surfaces. This periodic distortion propagates along the length of the body 100 to the output portion 114 with a corresponding decrease in amplitude and phase shift in proportion to the amount of sorbate sorbed by the surface 110.

The output transducer 104, which is similar to transducer 102, and comprises a pair of parallel conductive plates 122 disposed on opposite sides of the output portion 114 converts the periodic distortion into an alternating voltage. A pair of electrical conductors 124 connect the respective plates 118 to a pair of input terminals of the comparator 108 and apply the alternating voltage thereto. The output of the oscillator 106 is connected through an attenuator 126 to a reference input terminal of the comparator 108 by a conductor 127. The output of the comparator 108 is taken at an output terminal 128.

Referring also to FIGS. 6 and 7, an alternative embodiment of the acoustic body and input and output transducers of the device shown in FIG. 5 is illustrated. In this embodiment an elongated body 200 is formed from a material having acoustic transmission properties such as a metal. Alternatively, the material could be pyrex glass or quartz. As shown, the top and bottom surfaces and the front and rear surfaces of the body are parallel and the side are tapered to form respective knife edges 202. In cross section the body is hexagonal. The knife edges 202 lie on a nodal plane 204 (shown in dashed lines) passing through the middle of the body. The tapered sides serve to decouple the knife edges 202 from vibratory motion of the body 200. A transmitting crystal transducer 206 and a receiver crystal transducer 208 are cemented to the top surface of the body which is capable of sorbing an amount of sorbate. The transducer 206 is connected to an oscillator (not shown) and serves to drive the body in a shear vibration mode with a motional maxima at the top surface. This period distortion propagates along the length of the body 200 to the receiving transducer 208 with a corresponding decrease in amplitude and phase shift representative of the amount of sorbate sorbed by the top surface. With reference to FIG. 7 the edges of the body 200 are embedded in respective end supports 210 formed from a viscoelastic material. The end supports 210 serve to support the body and to damp out vibrations that reach the knife edges 202.

The embodiments thus far described provide a measurement of the absolute concentration of a preselected sorbate in the fluid stream. When it is desired to provide a measurement of the relative difference in the concentrations of two different sorbates dispersed in the fluid stream or of the same sorbate in two different streams, an embodiment of the present invention, schematically illustrated in FIG. 8, can be utilized. The fundamental difference in this embodiment is that it includes two similar circuits disposed in parallel in a fluid stream, each of the circuits being sensitive to a different sorbate.

With reference now to FIG. 8, an apparatus 129 includes an electronic oscillator 130, two similarly constructed circuits 132 and 134 connected to the output terminal of the oscillator and disposed in parallel in a fluid stream 136 in which different sorbates 138 and 140 are dispersed, and a phase comparator 135. The circuit 132 includes an input transducer 142, an acoustic transmission line 144 and an output transducer 146, and the circuit 134 includes an input transducer 148, an acoustic transmission line 150 and an output transducer 152. The outputs of the transducers 146 and 152 are connected to the inputs of comparator 135. The output of comparator 135 is taken at terminal 156. The circuits 132 and 134 differ in that the exterior surface of the transmission line 144 is coated with a film 158 that is capable of sorbing an amount of the sorbate 138 representative of its concentration in the fluid stream 136, and the exterior surface of the transmission line 150 is coated with a film 160 that is capable of sorbing an amount of the sorbate 140 representative of its concentration in the fluid stream 136.

In response to an alternating signal supplied by the oscillator 130, the transducers 142 and 148 convert the signal into acoustic energy and apply the energy to the respective inputs of the bodies forming the transmission lines 144 and 150. The energy propagates along the length of the respective bodies with a corresponding shift in phase in proportion to the amount of the sorbates 138 and 140 sorbed by the respective films 158 and 160. Transducers 146 and 152 convert the acoustic energy propagated to the output portions of the lines 144 and 150 into corresponding electrical signals. Comparator 135 compares the phase of the two electrical signals and develops an output signal on terminal 156 corresponding to the difference in concentration of the sorbates 138 and 140 in the fluid stream 136.

In yet another embodiment, a single acoustic transmission line may be used as shown in FIG. 9 to measure different sorbates in a common stream. As illustrated an acoustic transmission line 220 has a single transmitting transducer 222, two receiving transducers 224 and 226, and two comparators 228 and 230 connected to the respective outputs of the transducers 224 and 226 disposed thereon. The outputs of the comparators 228 and 230 are taken at terminals 232 and 234, respectively. An electronic oscillator 236 is connected to the inputs of the transducer 222 and the comparators 228 and 230. A film 238 that is capable of sorbing an amount of a first sorbate is coated on a portion of the exterior surface of the transmission line 220 between the transducers 222 and 224, and a film 240 that is capable of sorbing an amount of a second sorbate is coated on a portion of the exterior surface of the line 220 between the transducers 222 and 226.

The transmitting transducer 222, which may be an interdigital transducer, serves to propagate acoustic energy through the transmission line 220 in two directions, represented by the arrows 242 and 244, in response to an alternating-current signal supplied by the oscillator 236. The energy propagates along the length of the line in the two directions with a corresponding shift in phase in proportion to the amount of the two sorbates sorbed by the respective films 238 and 240. Transducers 224 and 226 convert the acoustic energy propagated thereto in corresponding electrical signals. The comparators 228 and 230 compare the phase of the respective electrical and oscillator signals and develop output signals on the respective terminals 232 and 234 corresponding to the concentrations of the sorbates in the fluid stream.

This embodiment may also be adapted to measure a common sorbate dispersed in different fluid streams and lends itself to applications requiring miniaturized measuring apparatus.

It should be recognized that the separation of the exciting, transmission and comparison functions in the apparatus enables the oscillator and the comparator to be optimized for stability and low noise, and the transmission line to be optimized for sensitivity, selectivity and response speed. In some embodiments it should be noted that various types transducers can be employed at the receiving end, that such transducers need not match the input transducer, and that optical sensors may be provided for sensing the motion of the body without loading the body. For example, the vibrations of the transmission line can be read out optically with a laser system such as the laser/doppler system of John Foster, described in U.S. Pat. No. 3,355,934.

While the invention has been particularly shown and described with reference to certain preferred embodiments, it will be understood by those skilled in the art that various alterations and modifications in the form and detail may be made therein. Accordingly, it is intended that the following claims cover all such alterations and modifications as fall within the true spirit and scope of the invention.

What is claimed is:

1. Apparatus for measuring a sorbate dispersed in a fluid stream comprising:
   a signal source means for generating an alternating-current signal;
   acoustic transmission line means for disposition in the fluid stream and including an elongated body having a surface capable of sorbing an amount of a first sorbate to be measured representative of the concentration thereof in the fluid stream, said body being capable of propagating acoustic energy along its length from one end portion to another end portion, the propagated acoustic energy being damped in amplitude and shifted in phase such that the change in amplitude or phase is proportional to the amount of sorbate sorbed by said surface;
   first transducing means for converting said alternating current signal to acoustic energy and for applying said acoustic energy to said one end portion;
   second transducing means for converting the acoustic energy propagated to said other end portion to a corresponding first electrical signal; and
   comparator means for comparing said first electrical signal to said alternating current signal and for developing an output signal corresponding to a difference therebetween, said output signal being indicative of the concentration of the sorbate in the fluid stream.

2. Apparatus for measuring a sorbate dispersed in a fluid stream as recited in claim 1 wherein said comparator means is a phase comparator.

3. Apparatus for measuring a sorbate dispersed in a fluid stream as recited in claim 1 wherein said comparator means is an amplitude comparator.

4. Apparatus for measuring a sorbate dispersed in a fluid stream as recited in claim 1 and further including means for attenuating said alternating current signal to an amplitude appropriate for comparison with said electrical signal.

5. Apparatus for measuring a sorbate dispersed in a fluid stream as recited in claim 1 and further including means for accumulating the output signal over a period of time and means responsive to the cumulative output signal and operative to provide an indication when said cumulative output signal exceeds a predetermined level.

6. Apparatus for measuring a sorbate dispersed in a fluid stream as recited in claim 1 wherein said surface is formed by an absorbent film disposed in covering relationship over said body, said film serving to absorb said sorbate.

7. Apparatus for measuring a sorbate dispersed in a fluid stream as recited in claim 1 wherein said body is formed from a material having a low temperature coefficient of propagation velocity and said first and second transducing means are interdigital transducer arrays formed on said surface.

8. Apparatus for measuring a sorbate dispersed in a fluid stream as recited in claim 1 wherein said elongated body is a block of material having a low temperature coefficient of propagation velocity, and wherein said first and second transducing means are crystals, when energized by said alternating current signal, said first crystal serves to periodically move and induce shear wave motion in said body, said second crystal being operative to respond to the wave motion propagated through said body and to produce said electrical signal.

9. Apparatus for measuring a sorbate dispersed in a fluid stream as recited in claim 8 wherein said body and said first and second transducing means are formed from a unitary block of piezoelectric material.

10. Apparatus for measuring a sorbate dispersed in a fluid stream as recited in claim 1 and further comprising:
    second acoustic transmission line means for disposition in the fluid stream and including a second elongated body having a second surface capable of sorbing an amount of a second sorbate to be measured representative of the concentration thereof in the fluid stream, said second body being capable of propagating acoustic energy along its length from one end portion to another end portion, the propagated acoustic energy being damped in amplitude and shifted in phase such that the change in amplitude or phase is proportional to the amount of the second sorbate sorbed by said second surface;
    third transducing means for converting said alternating-current signal to acoustic energy and for applying the acoustic energy to said one end portion of said second body; and
    fourth transducing means for converting the acoustic energy propagated to said other end portion of said second body to a corresponding second electrical signal for input to said comparator means, said comparator means serving to compare said first electrical signal and said second electrical signal and to develop an output signal corresponding to the difference in concentrations of the first and second sorbates in the fluid stream.

11. Apparatus for measuring a sorbate dispersed in a fluid stream as recited in claim 1 and further comprising:
    second acoustic transmission line means for disposition in a second fluid stream and including a second elongated body having a second surface capable to sorbing an amount of said sorbate to be measured representative of the concentration thereof in said second fluid stream, said second body being capable of propagating acoustic energy along its length from one end portion to another end portion, the propagated acoustic energy being damped in amplitude and shifted in phase such that the change in amplitude or phase is proportional to the amount of said sorbate sorbed by said second surface;
    third transducing means for converting said alternating-current signal to acoustic energy and for applying the acoustic energy to said one end portion of said second body; and
    fourth transducing means for converting the acoustic energy propagated to said other end portion of said second body to a corresponding second electrical signal for input to said comparator means, said comparator means serving to compare said first electrical signal and said second electrical signal and to develop an output signal corresponding to the difference in concentrations of said sorbate in said first and second fluid streams.

12. Apparatus for measuring first and second sorbates dispersed in a fluid stream comprising:

signal source means for generating an alternating-current signal;

acoustic transmission line means for disposition in the fluid stream and including an elongated body having a first surface capable of sorbing an amount of a first sorbate to be measured representative of the concentration thereof in the fluid stream, said body being capable of propagating acoustic energy along its length from a central portion to a first end portion, the propagated acoustic energy being damped in amplitude and shifted in phase such that the change in amplitude or phase is proportional to the amount of said first sorbate sorbed by said first surface, and having a second surface capable of sorbing an amount of a second sorbate to be measured representative of the concentration thereof in the fluid stream, said body being capable of propagating acoustic energy along its length from said central portion to a second end portion, such propagated energy being damped in amplitude and shifted in phase such that the change in amplitude or phase is proportional to the amount of said second sorbate sorbed by said second surface;

first transducing means for converting said alternating-current signal to acoustic energy and for applying said acoustic energy to said central portion;

second transducing means for converting the acoustic energy propagated to said first end portion to a corresponding first electrical signal;

third transducing means for converting the acoustic energy propagated to said second end portion to a corresponding second electrical signal;

first comparator means for comparing said first electrical signal to said alternating-current signal and for developing a first output signal corresponding to a difference therebetween, said first output signal being indicative of the concentration of said first sorbate in the fluid stream; and second comparator means for comparing said second electrical signal to said alternating-current signal and for developing a second output signal corresponding to a difference therebetween, said second output signal being indicative of the concentration of said second sorbate in the fluid stream.

13. Apparatus for measuring a sorbate dispersed in a fluid stream comprising:

signal source means for generating an alternating-current signal;

acoustic transmission line means for disposition in the fluid stream and including an elongated body having a surface capable of sorbing an amount of a first sorbate to be measured representative of the concentration thereof in the fluid stream, said body being capable of propagating acoustic energy along its length from one end portion to another end portion, the propagated acoustic energy being damped in amplitude and shifted in phase such that the change in amplitude or phase is proportional to the amount of sorbate sorbed by said surface;

first transducing means for converting said alternating current signal to acoustic energy and for applying said acoustic energy to said one end portion;

second transducing means for converting the acoustic energy propagated to said other end portion to a corresponding first electrical signal;

comparator means for comparing said first electrical signal to said alternating current signal and for developing an output signal corresponding to a difference therebetween, said output signal being indicative of the concentration of the sorbate in the fluid stream;

said body including a length of wire; and said first and second transducing means being magnetostrictive devices disposed around said wire at respective end portions thereof, said first magnetostrictive device serving to torsionally vibrate said wire and said second magnetostrictive device serving to convert the torsional vibrations propagated through said wire to said other end portion to a corresponding electrical signal.

* * * * *